US012611366B2

(12) United States Patent
Wu

(10) Patent No.: US 12,611,366 B2
(45) Date of Patent: Apr. 28, 2026

(54) PRE-MIXED STRONTIUM SILICATE-BASED BIOLOGICAL HYDRAULIC CEMENTING PASTE COMPOSITION, PREPARATION METHOD THEREFOR, AND APPLICATION THEREOF

(71) Applicants: Beijing C-ROOT Dental Medical Devices Co., Ltd., Beijing (CN); Bingmin Wu, Beijing (CN)

(72) Inventor: Bingmin Wu, Beijing (CN)

(73) Assignees: BEIJING C-ROOT DENTAL MEDICAL DEVICES CO., LTD., Beijing (CN); Bingmin Wu, Beijing (CN)

( * ) Notice: Subject to any disclaimer, the term of this patent is extended or adjusted under 35 U.S.C. 154(b) by 1387 days.

(21) Appl. No.: 17/266,102

(22) PCT Filed: Jul. 22, 2019

(86) PCT No.: PCT/CN2019/097075
§ 371 (c)(1),
(2) Date: Feb. 4, 2021

(87) PCT Pub. No.: WO2020/029785
PCT Pub. Date: Feb. 13, 2020

(65) Prior Publication Data
US 2021/0290495 A1     Sep. 23, 2021

(30) Foreign Application Priority Data
Aug. 9, 2018     (CN) .......................... 201810902541.1

(51) Int. Cl.
| | |
|---|---|
| *A61K 9/48* | (2006.01) |
| *A61K 6/54* | (2020.01) |
| *A61K 6/838* | (2020.01) |
| *A61K 6/853* | (2020.01) |

(52) U.S. Cl.
CPC ................ *A61K 6/853* (2020.01); *A61K 6/54* (2020.01); *A61K 6/838* (2020.01)

(58) Field of Classification Search
CPC .......... A61K 6/853; A61K 6/54; A61K 6/838; A61K 6/80; A61L 2400/06; A61L 27/10; A61L 27/12; A61L 27/50; A61L 2430/02; A61L 2430/12; A61L 27/025; A61L 27/52
See application file for complete search history.

(56) References Cited

U.S. PATENT DOCUMENTS

| | | | | |
|---|---|---|---|---|
| 5,348,475 A | * | 9/1994 | Waknine ................. | A61C 5/30 264/16 |
| 5,769,638 A | | 6/1998 | Torabinejad et al. | |
| 2006/0213395 A1 | | 9/2006 | Lu et al. | |
| 2008/0299093 A1 | | 12/2008 | Yang et al. | |

FOREIGN PATENT DOCUMENTS

| | | | |
|---|---|---|---|
| CN | 101124178 A | 2/2008 | |
| CN | 101668550 A | 3/2010 | |
| CN | 102049062 A | 5/2011 | |
| CN | 101668550 B | 2/2014 | |
| CN | 105311680 A | 2/2016 | |
| CN | 106031799 A | 10/2016 | |
| CN | 106620886 | 5/2017 | |
| CN | 108721693 A | 11/2018 | |
| SE | 1651271 A1 | 3/2018 | |
| WO | WO-2008128347 A1 * | 10/2008 | ........... A61K 6/0067 |
| WO | 2011139936 A2 | 11/2011 | |
| WO | 2011139936 A3 | 12/2011 | |

OTHER PUBLICATIONS

Machine translation of CN108721693A, publication date Nov. 2, 2018.*
Kim et al. (Mater. Sci. Eng. C 2014, 42, 665-671).*
Fredholm et al. (J. R. Soc. Interface 2012, 9, 880-889; see pp. 1-15).*
International search report issued for counterpart Chinese patent application No. PCT/CN2019/097075 mailed on Oct. 30, 2019.
First Office Action in corresponding Chinese Patent Application No. 201810902541.1 issued on Jul. 23, 2020.
Search Report in corresponding Chinese Patent Application No. 201810902541.1 issued on Jul. 23, 2020.
Xing, Min et al. "Bone tissue engineering strategy based on the synergistic effects of silicon and strontium ions", Acta Biomaterialia, vol. 72, (2018), pp. 381-395.
Extended European Search Report issued on Apr. 5, 2022 for counterpart European patent application No. 19847130.2.
Meili Zhang et al., "Synthesis, in vitro hydroxyapatite forming ability, and cytocompatibility of strontium silicate powders," Journal of Biomedical Materials Research Part B: Applied Biomaterials, vol. 93B, Issue 1, pp. 252-257 (2010).
Christie, JK, et al., "Effect of strontium inclusion on the bioactivity of phosphate-based glasses," Journal of Material Science, Kluwer Academic Publishers, Dordrecht, vol. 52, No. 15, pp. 9014-9022 (2017).

(Continued)

*Primary Examiner* — Michael G. Hartley
*Assistant Examiner* — Melissa J Perreira
(74) *Attorney, Agent, or Firm* — LOZA & LOZA, LLP; Michael Fedrick

(57) ABSTRACT

A pre-mixed strontium silicate-based biological hydraulic cement paste composition and preparation method and use thereof are disclosed. The pre-mixed strontium silicate-based biological hydraulic cement paste of the disclosure uses strontium silicate as the main phase and at least one non-aqueous solvent that is miscible with water, and preferably, it may further include at least one calcium phosphate compound and at least one radiopaque material, to prepare a biological hydraulic cement paste with excellent injectability. The material remains as a fluid under a sealed condition, and hydrates, solidifies and hardens when it is placed in a physiological environment and contacts with a physiological body fluid. The strontium silicate-based material having excellent biocompatibility and biological activity is used to prepare a pre-mixed strontium silicate-based cement paste, which can be used for medical and dental applications including fields of pulp capping, root canal therapy, dental restorations and the like.

12 Claims, 2 Drawing Sheets

(56)                     References Cited

OTHER PUBLICATIONS

First Office Action issued for corresponding Japanese Patent Application 2021-531162 mailed on Jun. 6, 2023.
Second Office Action issued for corresponding Japanese Patent Application 2021-531162 mailed on Nov. 7, 2023.

* cited by examiner

PRE-MIXED STRONTIUM SILICATE-BASED BIOLOGICAL HYDRAULIC CEMENTING PASTE COMPOSITION, PREPARATION METHOD THEREFOR, AND APPLICATION THEREOF

TECHNICAL FIELD

The disclosure relates to a hydraulic cement paste for biomedical applications, and more specifically, to a pre-mixed strontium silicate-based cement paste composition with biological hydraulic properties for use in osteology, dentistry and orthopedics applications, and preparation method and use thereof. The disclosure belongs to the field of medical technology.

BACKGROUND

It is well known that strontium silicate and calcium silicate can be hydrated when mixed with water, and solidify and harden by precipitating colloidal strontium silicate and calcium silicate hydrates (Sr—S—H, C—S—H), similar to ordinary Portland cement (OPC).

These silicate-based bio-cement materials have good applications in the biomedical field, especially as dental filling materials in dental clinics, and have been widely used. An ideal dental filling material must have good biocompatibility, antibacterial properties and clinical operability. In addition, biological activity is considered as a basis for measuring the performance of materials bonding to tooth body. Therefore, bio-cement materials have also received more and more attention from dentists and researchers.

At present, the most widely used calcium silicate-based material in dental filling materials is Mineral Trioxide Aggregate (MTA). Mahmoud Torabinejad first disclosed a method of repairing tooth cavities with MTA materials in 1998 (U.S. Pat. No. 5,769,638). The main components of the MTA material are tricalcium silicate and dicalcium silicate, which are similar to Portland cement and can be used in root canal filling materials, but the formulation is troublesome and also causes waste. The Chinese patent application (application number CN200880011743.1) entitled "Pre-mixed biological hydraulic cement paste composition and use thereof" discloses a pre-mixed cement paste that can be used for medical or dental applications. In this patent, tricalcium silicate, dicalcium silicate and an organic solvent are premixed. This is convenient for doctors to use, but the setting time is too long, which needs 72 hours to solidify in some cases. Too long setting time not only causes the patient to wait longer, but also makes the surgical procedure more complicated.

The Chinese patent application (application number CN200910197934.8) entitled "Injectable efficient suspended stable calcium phosphate cement and preparation method and use thereof" discloses an injectable calcium phosphate cement material system. This patent improves the suspension stability of the calcium phosphate cement premix system by adding fumed silica and modified product thereof. The disadvantage is that the calcium phosphate cement has insufficient strength and is easily broken.

Therefore, it is of great significance to further develop a pre-mixed biological hydraulic cement paste with short setting time, high biological activity, sufficient compressive strength and good clinical operability.

Strontium is an indispensable microelement in the human body, and it is a normal part of human bones and teeth. The normal concentration of strontium in human bones is 360 ppm, and 99.0% of the strontium in vivo is present in bones and teeth. The main function of strontium on the human body is closely related to the formation of bones. Studies have shown that strontium can regulate the differentiation of MSCS (marrow mesenchymal stem cells) into osteoblasts and promote the synthesis and precipitation of bone matrix proteins. Therefore, strontium can promote osteoblast differentiation and osteogenesis. Strontium can also substitute a small amount of calcium in hydroxyapatite crystals in calcified tissue bones and teeth. The substitution with a small amount of strontium element can reduce lattice defects, make the arrangement of atoms closer, and produce a certain strengthening effect, thereby improving the bone strength of the teeth. While the strontium silicate hydrate (Sr—S—H) composite hydroxyapatite composition plays the role of filling and sealing, it has better biocompatibility, and functions to promote bone formation and improve bone strength, compared with calcium silicate hydrate (C—S—H).

SUMMARY OF THE INVENTION

An object of the disclosure is to provide a pre-mixed strontium silicate-based biological hydraulic cement paste composition with short setting time, high biological activity and good clinical operability.

In order to achieve the above object, the disclosure adopts the following technical means.

The disclosure provides a pre-mixed strontium silicate-based cement paste composition, including:
- component (a): at least one strontium silicate compound, wherein the strontium silicate compound is preferably selected from strontium silicate, tristrontium silicate, distrontium silicate, and mixtures thereof; and
- component (b): at least one substantially anhydrous liquid carrier mixed with the at least one strontium silicate compound, wherein the substantially anhydrous liquid carrier is preferably selected from ethylene glycol, propylene glycol, polyethylene glycol, liquid glycerin, ethanol, a silicone oil, clove oil, an animal oil, a vegetable oil, an organic acid, and mixtures thereof.

According to a particular embodiment of the disclosure, preferably, in the pre-mixed strontium silicate-based cement paste composition, the solid component (a) accounts for 60%-92% of the total mass of the cement paste composition, and the liquid component (b) accounts for 8%-40% of the total mass of the cement paste composition.

According to a particular embodiment of the disclosure, preferably, the strontium silicate-based cement paste composition further includes:
- component (c): at least one radiopaque material.

According to a particular embodiment of the disclosure, preferably, the radiopaque material is selected from at least one of zirconium oxide, bismuth oxide and tantalum oxide.

According to a particular embodiment of the disclosure, preferably, in the pre-mixed strontium silicate-based cement paste composition, the solid components (a) and (c) account for 60%-92% of the total mass of the cement paste composition, and the liquid component (b) accounts for 8%-40% of the total mass of the cement paste composition. Further preferably, in the pre-mixed strontium silicate-based cement paste composition, the solid component (a) accounts for 20%-82% of the total mass of the cement paste composition, the solid component (c) accounts for 10%-40% of the total mass of the cement paste composition, and the liquid component (b) accounts for 8%-40% of the total mass of the cement paste composition.

According to a particular embodiment of the disclosure, preferably, in addition to components (a) and (b) or components (a), (b) and (c), the strontium silicate-based cement paste composition further includes: component (d): at least one calcium phosphate compound.

According to a particular embodiment of the disclosure, preferably, the calcium phosphate compound is selected from at least one of tricalcium phosphate, tetracalcium phosphate, calcium dihydrogen phosphate and hydroxyapatite.

According to a particular embodiment of the disclosure, preferably, in the pre-mixed strontium silicate-based cement paste composition, the solid components (a), (c) and (d) account for 60%-92% of the total mass of the cement paste composition, and the liquid component (b) accounts for 8%-40% of the total mass of the cement paste composition. Further preferably, in the pre-mixed strontium silicate-based cement paste composition, the solid component (a) accounts for 10%-42% of the total mass of the cement paste composition, the solid component (c) accounts for 10%-40% of the total mass of the cement paste composition, the solid component (d) accounts for 10%-40% of the total mass of the cement paste composition, and the liquid component (b) accounts for 8%-40% of the total mass of the cement paste composition.

The pre-mixed strontium silicate-based cement paste composition provided by the disclosure can be prepared according to the following steps:

placing components into a glass container sequentially, mechanically mixing with a stainless-steel stirring rod and thoroughly blending; and subsequently, transferring the mixed paste to a medical syringe equipped with an injection hose needle, to obtain a suspended stable pre-mixed strontium silicate-based cement paste.

Further, the disclosure also provides use of the pre-mixed strontium silicate-based cement paste composition in the preparation of filling materials for osteology or dentistry.

The pre-mixed strontium silicate-based biological hydraulic cement paste of the disclosure uses strontium silicate as the main phase and at least one non-aqueous solvent that is miscible with water, and preferably, it may further include at least one calcium phosphate and at least one radiopaque material, to prepare a biological hydraulic cement paste with excellent injectability. The material remains as a fluid under a sealed condition, and hydrates, solidifies and hardens when it is filled into bones or teeth and contacts with physiological body fluids. The strontium silicate-based material having excellent biocompatibility and biological activity is used to prepare a strontium silicate-based biological hydraulic cement paste, which can be used for medical applications, especially as a filling material for use in the fields of pulp capping, root canal therapy, dental restorations and the like.

Compared with the prior art, the disclosure has the following advantages:

(1) The pre-mixed strontium silicate-based cement paste of the disclosure has a short setting time and is convenient for doctors to operate, and the temperature rise during reaction is not obvious, as compared with calcium phosphate cements, t;

(2) Compared with pre-mixed calcium silicate dental filling materials, the pre-mixed strontium silicate-based cement paste of the disclosure has the following advantages:

(A) fast setting.

(B) strontium silicate having better biocompatibility than calcium silicate, and easy to form hydroxyapatite that promotes bone formation when used in combination with calcium phosphate;

(C) improved bone strength. For example, it can be seen from FIG. 3 that the hydration products of strontium silicate are mostly dense small pom-like microstructures; the needle-like hydration product is smaller and has a good cross-linking degree and a denser structure similar to the hydroxyapatite pom-like structure. Therefore, the material has better strength and toughness and good biocompatibility. Moreover, by adjusting the ratio of calcium phosphate and strontium silicate, different requirements can be met. If it is adjusted to 30-40 MPa, it can be used for root canal filling material, which has lower strength than calcium silicate paste and can be used for retreatment; if it is adjusted to be harder, it can be used for repair.

(D) Strontium is an indispensable microelement in the human body and can promote osteoblast differentiation and bone formation. Strontium can also substitute small amounts of calcium in hydroxyapatite crystals in calcified tissue bones and teeth. The use of strontium silicate can supplement strontium elements, reduce tooth lattice defects, thereby improving the bone strength of teeth.

DETAILED DESCRIPTION FOR THE INVENTION

Figure 1:
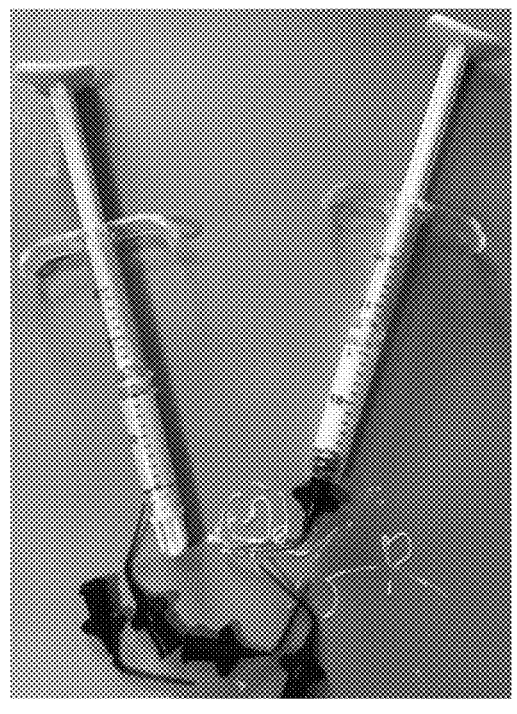
FIG. 1 shows the pre-mixed strontium silicate-based cement paste material obtained in Example 1.

The disclosure will be further described below in conjunction with specific examples, and the advantages and features of the disclosure will become clearer with the description. However, the examples are only exemplary and do not constitute any limitation to the scope of the disclosure. Those skilled in the art should understand that the details and forms of the technical solution of the disclosure can be modified or replaced without departing from the spirit and scope of the disclosure, but these modifications and replacements fall within the protection scope of the disclosure.

Test Method for Setting Time

1. Equipments 1.1. Constant temperature and humidity chamber: an environment with a temperature of 37° C.±1° C. and a relative humidity of not less than 95% is maintained.

1.2. Penetrometer: a flat end face indenter with a mass of 100 g±0.5 g and a diameter of 2 mm±0.1 mm: the tip of the indenter is a cylinder with a length of at least 5 mm, and the end face of the indenter should be a horizontal plane at right angles to the long axis.

1.3 Mold: a stainless-steel ring mold; the mold cavity has an inner diameter d=10 mm and a height h=2 mm.

1.4. Metal block: minimum size 8 mm×20 mm×10 mm, placed in the constant temperature and humidity chamber at 37° C.±1° C. for at least 1 h before use.

1.5. Flat glass sheet: about 1 mm thick, for example, glass slide.

2. Sample Preparation

The stainless-steel mold was placed on the flat glass sheet and was filled with the blended root canal filling paste (i.e., the suspended stable pre-mixed strontium silicate-based cement paste prepared in the examples). The material was level with the upper end of the mold. After the completion of blending, the above components were placed on the metal block in the constant temperature and humidity chamber.

3. Steps

After curing for 8 h, the sample was taken out every 1 hour. The indenter of the penetrometer was gently and vertically placed on the horizontal surface of the root canal filling paste, raised and wiped clean. The above operations were repeated until no indentation can be seen with naked eyes. The period starting from the end of the blending, until the indentation no longer appears is recorded as the setting time.

4. Results

The setting time was recorded when there is no indentation.

Example 1 Preparation of a Suspended Stable Pre-Mixed Strontium Silicate-Based Cement Paste (1) weighing the raw materials according to the following weight percentages:

component (a): 55% of tristrontium silicate;
component (b): 22% of polyethylene glycol; and
component (c): 23% of zirconium oxide;

(2) placing the components (a), (c) and (b) of step (1) into a glass container sequentially, mechanically mixing with a stainless-steel stirring rod, and thoroughly blending for 10 min;

(3) subsequently, transferring the mixed paste to a medical syringe equipped with an injection hose needle, to obtain the suspended stable pre-mixed strontium silicate-based cement paste.

The material remains as a fluid under sealed conditions. The sample is extruded and placed into a constant temperature and humidity chamber at 37° C. and a humidity of 95% or more (or filled into the teeth in contact with physiological body fluids) for hydration, solidification and hardening. Setting time: 13 hours.

Figure 2:
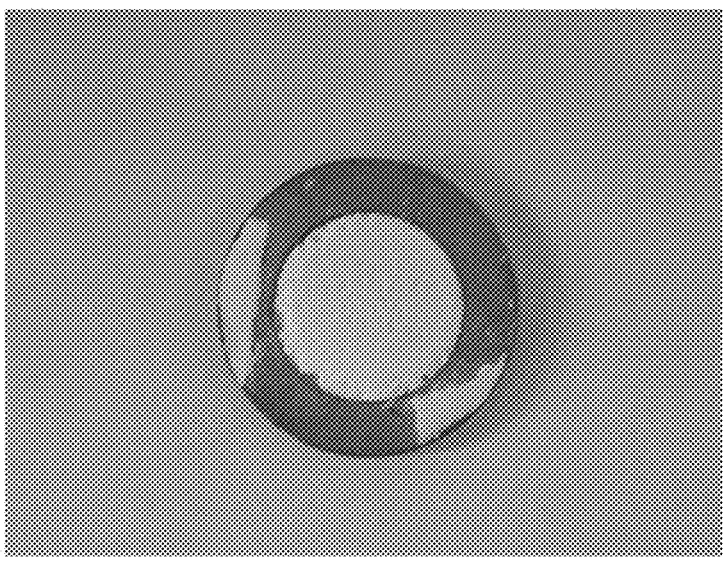
FIG. 2 is a photograph of the strontium silicate-based cement paste obtained in Example 1 after hydraulic setting.
Figure 3:
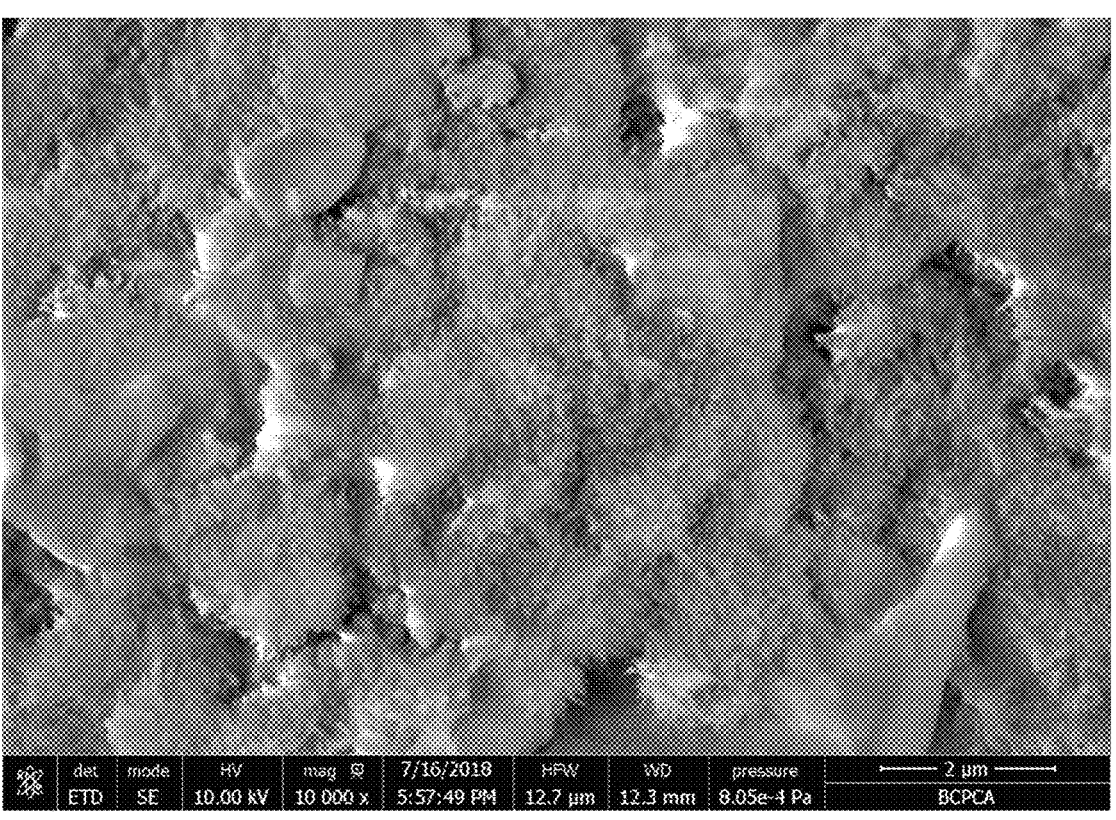
FIG. 3 is a micrograph of the material obtained in Example 1 after hydraulic setting.
Figure 4:
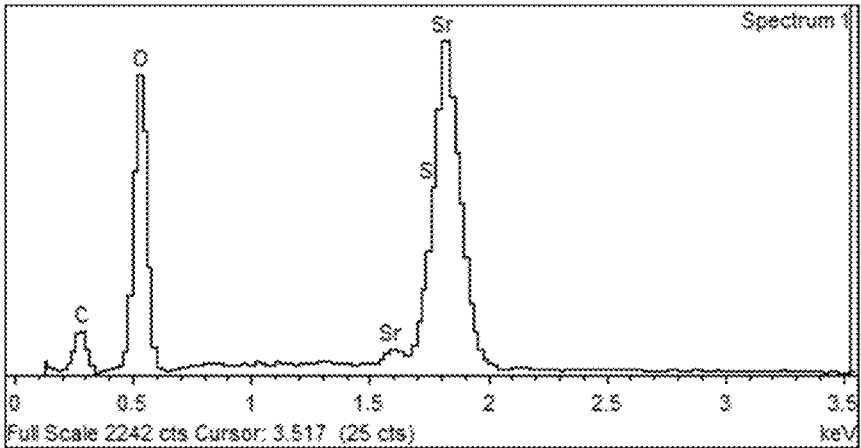
FIG. 4 is an XRD element analysis diagram of the material obtained in Example 1 after hydraulic setting.

FIG. 1 shows the pre-mixed strontium silicate-based cement paste material obtained in Example 1. FIG. 2 is a photograph of the strontium silicate-based cement paste obtained in Example 1 after hydraulic setting. FIG. 3 is a micrograph of the material obtained in Example 1 after hydraulic setting. FIG. 3 shows that the needle-like tissues on small pom-like structure of the strontium silicate hydration product Sr—S—H are fine and dense, interlaced, and crosslinked together to form a dense, high-strength microstructure, which is very similar to the hydroxyapatite pom-shaped structure and has good mechanical properties. FIG. 4 is an XRD element analysis diagram of the material obtained in Example 1 after hydraulic setting. FIG. 4 shows that the strontium silicate hydrate (Sr—S—H) is mainly composed of Sr, Si, and O elements (note: H element is not shown in XRD analysis of electron microscope). Strontium has a good effect on strengthening teeth and bones.

The pre-mixed strontium silicate-based cement paste material obtained in Example 1 was placed in a constant temperature and humidity chamber at 37° C. and a humidity of 95% for hydration test. The material was taken out at 0.5, 1, 2, 3, 5, 8, 12, 24, and 48 hours after being placed in, and measured with an infrared thermometer. The temperature was 37.0° C., 36.8° C., 37.1° C., 36.9° C., 37.0° C., 37.0° C., 36.6° C., 37.1° C., and 37.0° C., respectively. The temperature was substantially unchanged, indicating that the pre-mixed strontium silicate-based cement paste material prepared in Example 1 has an effect that the temperature rise during reaction is not significant.

Example 2 Preparation of a Suspended Stable Pre-Mixed Strontium Silicate-Based Cement Paste (1) weighing the raw materials according to the following weight percentages:

component (a): 18% of tristrontium silicate;
component (b): 27% of polyethylene glycol;
component (c): 30% of tantalum oxide; and
component (d): 16% of anhydrous calcium dihydrogen phosphate and 9% of tetracalcium phosphate;

(2) placing the components (a), (c), (d) and (b) of step (1) into a glass container sequentially, mechanically mixing with a stainless-steel stirring rod, and thoroughly blending for 10 min;

(3) subsequently, transferring the mixed paste to a medical syringe equipped with an injection hose needle, to obtain the suspended stable pre-mixed strontium silicate-based cement paste 2.

The material remains as a fluid under sealed conditions. The sample is extruded and placed into a constant temperature and humidity chamber at 37° C. and a humidity of 95% or more (or filled into the teeth in contact with physiological body fluids) for hydration, solidification and hardening. Setting time: 13 hours.

The pre-mixed strontium silicate-based cement paste material obtained in Example 2 was placed in a constant temperature and humidity chamber at 37° C. and a humidity of 95% for hydration test. The material was taken out at 0.5, 1, 2, 3, 5, 8, 12, 24, and 48 hours after being placed in, and measured with an infrared thermometer. The temperature was substantially unchanged in the range of 36-38° C., indicating that the pre-mixed strontium silicate-based cement paste material prepared in Example 2 has an effect that the temperature rise during reaction is not significant.

Example 3 Preparation of a Suspended Stable Pre-Mixed Strontium Silicate-Based Cement Paste (1) weighing the raw materials according to the following weight percentages:

component (a): 12% of tristrontium silicate and 7% of distrontium silicate;
component (b): 29% of glycerin;
component (c): 32% of bismuth trioxide; and
component (d): 20% of calcium dihydrogen phosphate;

(2) placing the components (a), (c), (d) and (b) of step (1) into a glass container sequentially, mechanically mixing with a stainless-steel stirring rod, and thoroughly blending for 10 min;

(3) subsequently, transferring the mixed paste to a medical syringe equipped with an injection hose needle, to obtain the suspended stable pre-mixed strontium silicate-based cement paste 3.

The material remains as a fluid under sealed conditions. The sample is extruded and placed into a constant temperature and humidity chamber at 37° C. and a humidity of 95% or more (or filled into the teeth in contact with physiological body fluids) for hydration, solidification and hardening. Setting time: 18 hours.

The pre-mixed strontium silicate-based cement paste material obtained in Example 3 was placed in a constant temperature and humidity chamber at 37° C. and a humidity of 95% for hydration test. The material was taken out at 0.5, 1, 2, 3, 5, 8, 12, 24, and 48 hours after being placed in, and measured with an infrared thermometer. The temperature was substantially unchanged in the range of 36-38° C., indicating that the pre-mixed strontium silicate-based cement paste material prepared in Example 3 has an effect that the temperature rise during reaction is not significant.

Example 4 Preparation of a Suspended Stable Pre-Mixed Strontium Silicate-Based Cement Paste (1) weighing the raw materials according to the following weight percentages:

component (a): 65% of tristrontium silicate; and component (b): 35% of polyethylene glycol:

(2) placing the components (a) and (b) of step (1) into a glass container sequentially, mechanically mixing with a stainless-steel stirring rod, and thoroughly blending for 10 min:

(3) subsequently, transferring the mixed paste to a medical syringe equipped with an injection hose needle, to obtain the suspended stable pre-mixed strontium silicate-based cement paste 4.

The material remains as a fluid under sealed conditions. The sample is extruded and placed into a constant temperature and humidity chamber at 37° C. and a humidity of 95% or more (or filled into the teeth in contact with physiological body fluids) for hydration, solidification and hardening. Setting time: 12 hours.

The pre-mixed strontium silicate-based cement paste material obtained in Example 4 was placed in a constant temperature and humidity chamber at 37° C. and a humidity of 95% for hydration test. The material was taken out at 0.5, 1, 2, 3, 5, 8, 12, 24, and 48 hours after being placed in, and measured with an infrared thermometer. The temperature was substantially unchanged around 37° C., indicating that the pre-mixed strontium silicate-based cement paste material prepared in Example 4 has an effect that the temperature rise during reaction is not significant.

What is claimed is:

1. A pre-mixed strontium silicate-based cement paste composition, wherein, the pre-mixed strontium silicate-based cement paste composition includes:

component (a): at least one strontium silicate compound; and component (b): at least one substantially anhydrous liquid carrier mixed with the at least one strontium silicate compound, wherein, in the pre-mixed strontium silicate-based cement paste composition, component (a) is a solid component which accounts for 60%-92% of the total mass of the cement paste composition, and component (b) is a liquid component which accounts for 8%-40% of the total mass of the cement paste composition, wherein the strontium silicate compound is selected from the group consisting of tristrontium silicate, distrontium silicate, and mixtures thereof, and wherein the substantially anhydrous liquid carrier is selected from the group consisting of ethylene glycol, propylene glycol, polyethylene glycol, liquid glycerin, ethanol, a silicone oil, clove oil, an animal oil, a vegetable oil, an organic acid, and mixtures thereof.

2. The pre-mixed strontium silicate-based cement paste composition according to claim 1, wherein, the strontium silicate-based cement paste composition further includes:

component (c): at least one radiopaque material.

3. The pre-mixed strontium silicate-based cement paste composition according to claim 2, wherein, the radiopaque material is selected from at least one of zirconium oxide, bismuth oxide and tantalum oxide.

4. The pre-mixed strontium silicate-based cement paste composition according to claim 2, wherein, in the pre-mixed strontium silicate-based cement paste composition, components (a) and (c) are solid components which account for 60%-92% of the total mass of the cement paste composition, and the liquid component (b) accounts for 8%-40% of the total mass of the cement paste composition.

5. The pre-mixed strontium silicate-based cement paste composition according to claim 1, wherein, the strontium silicate-based cement paste composition further includes:

component (d): at least one calcium phosphate compound.

6. The pre-mixed strontium silicate-based cement paste composition according to claim 5, wherein, the calcium phosphate compound is selected from at least one of tricalcium phosphate, tetracalcium phosphate, calcium dihydrogen phosphate and hydroxyapatite.

7. The pre-mixed strontium silicate-based cement paste composition according to claim 5, wherein, in the pre-mixed strontium silicate-based cement paste composition, components (a) and (d) are solids which account for 60%-92% of the total mass of the cement paste composition, and the liquid component (b) accounts for 8%-40% of the total mass of the cement paste composition.

8. The pre-mixed strontium silicate-based cement paste composition according to claim 2, wherein, the strontium silicate-based cement paste composition further includes:

component (d): at least one calcium phosphate compound.

9. The pre-mixed strontium silicate-based cement paste composition according to claim 8, wherein, the calcium phosphate compound is selected from at least one of tricalcium phosphate, tetracalcium phosphate, calcium dihydrogen phosphate and hydroxyapatite.

10. The pre-mixed strontium silicate-based cement paste composition according to claim 8, wherein, in the pre-mixed strontium silicate-based cement paste composition, components (a), (c) and (d) are solids which account for 60%-92% of the total mass of the cement paste composition, and the liquid component (b) accounts for 8%-40% of the total mass of the cement paste composition.

11. A method of treating a tooth or bone of a subject, comprising the steps of:

obtaining the pre-mixed strontium silicate-based cement paste composition of claim 1; and applying the pre-mixed strontium silicate-based cement paste composition to the tooth or bone of the subject.

12. A pre-mixed strontium silicate-based cement paste composition, wherein the pre-mixed strontium silicate-based cement paste composition includes:

component (a): at least one strontium silicate compound; and component (b): at least one substantially anhydrous liquid carrier mixed with the at least one strontium silicate compound, wherein the strontium silicate compound is selected from the group consisting of tristrontium silicate, distrontium silicate, and mixtures thereof and is present in the composition in an amount of between 18% and 65% by weight, and wherein the substantially anhydrous liquid carrier is selected from the group consisting of ethylene glycol, propylene glycol, polyethylene glycol, liquid glycerin, ethanol, a silicone oil, clove oil, an animal oil, a vegetable oil, an organic acid, and mixtures thereof and is present in the composition in an amount of between 22% and 35% by weight.

\* \* \* \* \*